(12) United States Patent
Dorsch et al.

(10) Patent No.: US 7,687,624 B2
(45) Date of Patent: Mar. 30, 2010

(54) PROCESS FOR THE PRODUCTION OF N-ARYLMORPHOLINONES

(75) Inventors: Dieter Dorsch, Ober-Ramstadt (DE); Bertram Cezanne, Mörfelden-Walldorf (DE); Werner Mederski, Zwingenberg (DE); Christos Tsaklakidis, Weinheim (DE); Hanns Wurziger, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 1074 days.

(21) Appl. No.: 10/567,848

(22) PCT Filed: Jul. 16, 2004

(86) PCT No.: PCT/EP2004/007938

§ 371 (c)(1),
(2), (4) Date: Feb. 10, 2006

(87) PCT Pub. No.: WO2005/016899

PCT Pub. Date: Feb. 24, 2005

(65) Prior Publication Data

US 2006/0217550 A1 Sep. 28, 2006

(30) Foreign Application Priority Data

Aug. 11, 2003 (DE) ................................ 103 36 716

(51) Int. Cl.
*C07D 295/073* (2006.01)
*C07D 295/10* (2006.01)
(52) U.S. Cl. ...................................................... 544/166
(58) Field of Classification Search ................... 544/166
See application file for complete search history.

(56) References Cited

U.S. PATENT DOCUMENTS

2004/0087582 A1 5/2004 Dorsch et al.

FOREIGN PATENT DOCUMENTS

WO WO 02057236 7/2002

OTHER PUBLICATIONS

Astle, M.J.; Welks, J.D.: J. Org. Chem., Bd. 26, 1961. 4325-4327, XP002303446.
Database Caplus 'Online! Chemical Abstracts Service, Columbus, Ohio, US; Tulyaganov, S. R. et al: "Reaction of some N-(2-hydroxyalkyl)arylamines with monochloroacetic acid derivatives" retrieved from STN Database accession No. 1970:466523 XP002303444.

*Primary Examiner*—Rebecca L Anderson
(74) *Attorney, Agent, or Firm*—Millen, White, Zelano & Branigan, P.C.

(57) ABSTRACT

The invention relates to a method for production of compounds of formula (I), where X has the meaning given in claim 1 and precursors for the same.

13 Claims, No Drawings

PROCESS FOR THE PRODUCTION OF N-ARYLMORPHOLINONES

This application is a 371 of PCT/EP04/07938 filed Jul. 16, 2004.

The invention relates to a process for the preparation of compounds of the formula I

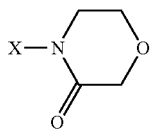

in which

X denotes

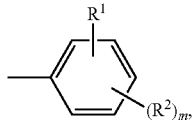

$R^1$ denotes $NO_2$, CN, $COOR^3$, $CON(R^3)_2$, $COR^3$, $SO_2R^4$, $SO_2N(R^3)_2$, $CF_3$, F or Cl, $R^2$ denotes H, Hal, A, $OR^3$, $N(R^3)_2$, $NO_2$, CN, $COOR^3$, CON$(R^3)_2$, $NR^3COA$, $NR^3CON(R^3)_2$, $NR^3COOR^3$, $NR^3SO_2A$, —$[C(R^5)_2]_n$—Ar, —$[C(R^5)_2]_n$-Het, —$[C(R^5)_2]_n$-cycloalkyl, $COR^3$, $SO_2N(R^3)_2$ or $SO_2R^4$, $R^3$ denotes H, A, —$[C(R^5)_2]_n$—Ar or —$[C(R^5)_2]_n$-Het, $R^4$ denotes A, —$[C(R^5)_2]_n$—Ar or —$[C(R^5)_2]_n$-Het, $R^5$ denotes H or A', Ar denotes phenyl which is unsubstituted or mono-, di- or trisubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ or $S(O)_nA$, Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O), A' denotes unbranched or branched alkyl having 1-6 C atoms, A denotes unbranched, branched or cylic alkyl having 1-12 C atoms, in which one or two $CH_2$ groups may be replaced by O or S atoms and/or by —CH=CH— groups and/or in addition 1-7H atoms may be replaced by F, Hal denotes F, Cl, Br or I, n denotes 0, 1 or 2, m denotes 0, 1, 2, 3 or 4, and salts thereof, characterised in that a) a compound of the formula II $$X-NH_2 \quad\quad II$$

in which

X has the meaning indicated above, is reacted with 5-chloro-2,3-dihydro-1,4-dioxin

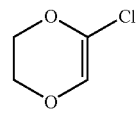

to give a compound of the formula III

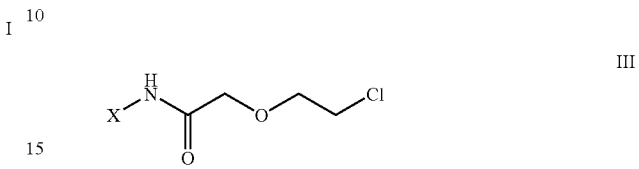

in which

X has the meaning indicated above, b) then a compound of the formula III is cyclised to give a compound of the formula I, and c) the latter is optionally converted into its salt by converting a base or acid of the formula I into one of its salts.

The invention had the object of finding novel improved processes for the preparation of precursors of factor Xa inhibitors.

Compared with known processes from the prior art, the process according to the invention is shorter and more efficient.

Factor Xa inhibitors can be employed for combating and preventing thromboembolic diseases, such as thrombosis, myocardial infarction, arteriosclerosis, inflammation, apoplexy, angina pectoris, restenosis after angioplasty and claudicatio intermittens.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin. The inhibition of factor Xa and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59. The publications listed below describe an antitumoural action of TF-VII and factor Xa inhibitors for various types of tumour:

K. M. Donnelly et al. in Thromb. Haemost. 1998; 79: 1041-1047;

E. G. Fischer et al. in J. Clin. Invest. 104: 1213-1221 (1999);

B. M. Mueller et al. in J. Clin. Invest. 101: 1372-1378 (1998);

M. E. Bromberg et al. in Thromb. Haemost. 1999; 82: 88-92.

WO 02/057236 describes other processes and morpholinone precursors.

The following methods for the preparation of 2-(2-chloroethoxy)acetamides are known in the literature:

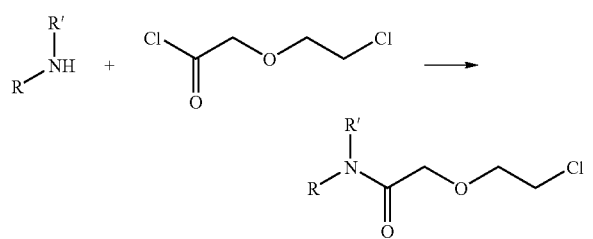

This method is described, for example, in U.S. Pat. No. 3,074,939, BE 776767 and DE 1922613.

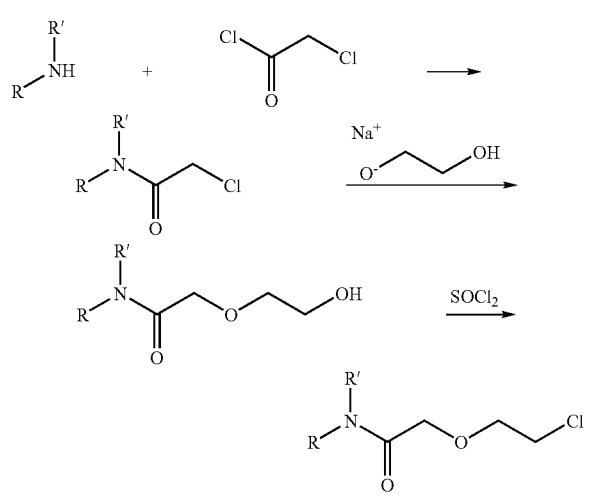

This method is described, for example, in G. May, D. Peteri, Arzneim.-Forsch. (Drug Res.) 23, 718 (1973).

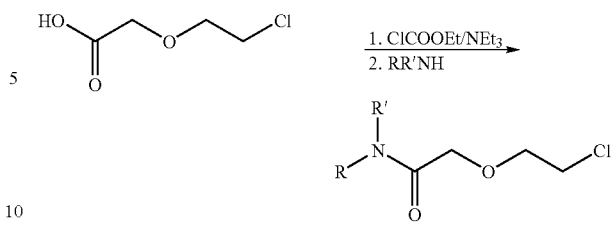

This method is described, for example, in DE 2150075.

However, these methods have disadvantages. Thus, many reaction steps are necessary or the starting materials are expensive.

M. J. Astle, J. D. Welks, J. Org. Chem. 26, 4325 (1961) disclose the following reaction:

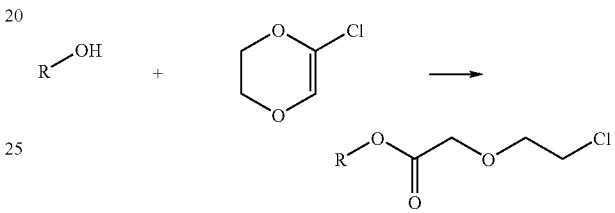

R = alkyl, phenyl

We have found, surprisingly, that arylamines, so long as they have a $pK_a$ of less than or equal to 3, also react with 2-chlorodioxene to give 2-(2-chloroethoxy)acetamides.

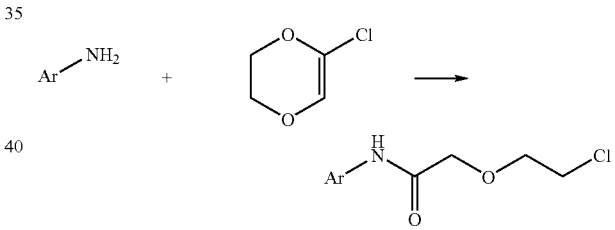

In view of M. J. Astle, J. D. Welks, J. Org. Chem. 26, 4325 (1961), this is unexpected since amines, such as ammonia, benzylamine, 8-aminoquinoline or 4-methoxyaniline, do not react or react very poorly.

Comparison of $pK_a$ values:

| | |
|---|---|
| Benzylamine | 9.5 |
| Ammonia | 9.24 |
| 8-Aminoquinoline | 0.7 (NH2 group) and 4.0 (quinoline nitrogen). The basic quinoline nitrogen prevents the reaction. |
| 4-Methoxyaniline | 5.4 |
| 4-Nitroaniline | 1.0 |
| 4-Cyanoaniline | 1.7 |
| 3-Nitroaniline | 2.5 |
| 2-Methyl-4-nitroaniline | 1.04 |
| Methyl 4-aminobenzoate | 1.5 |
| 4-Aminobenzophenone | 2.2 |
| 2-Nitroaniline | −0.23 |

In the reaction, it is advantageous to add an acid, for example a Brönsted acid, such as hydrochloric acid, or a Lewis acid, or alternatively to add 2,2-dichlorodioxene, a compound which, as is known from the literature (R. K. Summerbell, H. E. Lunk, J. Am. Chem. Soc. 79, p. 4802, 1957), readily dissociates into hydrogen chloride and 2-chlorodioxene. The reaction can be carried out in many solvents, for example toluene, acetonitrile, dioxane, but also in mass, i.e. without solvent. Typical reaction temperatures are 0 to 150° C., generally around 80° C., for example between 70 and 90° C.

The advantage of this process lies in the ready accessibility of 2-chlorodioxene or 2,2-dichlorodioxane.

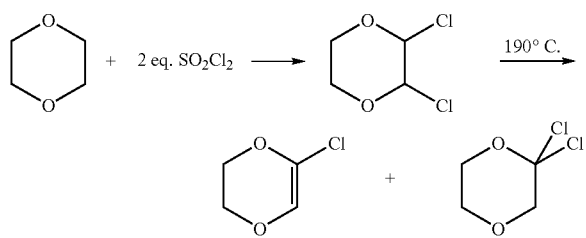

The preparation of 2,3-dichlorodioxane is described, for example, in M. Iyoda et al, Heterocycles, 54, p. 833, 2001. The thermal elimination of hydrogen chloride is described in U.S. Pat. No. 2,756,240. This method gives 2-chlorodioxene, which is contaminated with a certain proportion of 2,2-dichlorodioxane (typically 5 to 50%).

N. V. Kuznetsov, I. I. Krasavtsev, Sov. Prog. Chem. (Engl. Transl.) 44, p. 77, 1987, describe methods for the preparation of 2-chlorodioxene from 2,3-dichlorodioxane using sodium hydroxide.

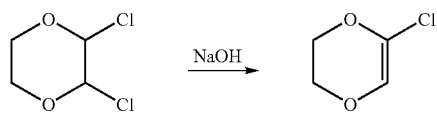

The cyclisation of chloroethoxyacetamides to give morpholinones has hitherto only been described in two publications, in DE 922613 and L. Fumagalli et al. Pharmazie 30, 78 (1975).

Both cases involve triiodobenzoic acid and triiodophenylalkanoic acid derivatives.

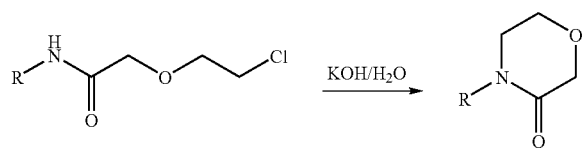

However, this process is only suitable for substrates which are watersoluble, as in the above documents, in which R always contains a free carboxyl group.

We have found that chloroethoxyacetamides can preferably be cyclised to give morpholinones using weak bases, such as, for example, caesium carbonate or potassium carbonate, in a suitable solvent, such as, for example, acetonitrile.

Above and below, A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl or trifluoromethyl.

A' preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl or trifluoromethyl.

Cycloalkyl has 3-7 C atoms and preferably denotes cyclopropyl, cyclobutyl, cyclopentyl or cylohexyl.

Hal preferably denotes F, Cl or Br, but also I.

$R^1$ preferably denotes $NO_2$, CN, COOH, $COOR^3$, $COR^3$ or Cl.

$R^2$ preferably denotes H, Hal or A.

$R^3$ preferably denotes H, A' or $—[C(R^5)_2]_n—Ar$.

$R^4$ preferably denotes A.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^5$, $SO_2A$, $COOR^5$ or CN.

Ar particularly preferably denotes, for example, phenyl which is unsubstituted or mono- or disubstituted by Hal, A, OA, $SO_2A$, $SO_2NH_2$, $COOR^5$ or CN, such as, for example, phenyl, 2-methylsulfonylphenyl, 2-aminosulfonylphenyl, 2-, 3- or 4-chlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl or 4-ethoxycarbonylphenyl.

Ar very particularly preferably denotes unsubstituted phenyl.

Het is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O) and denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

n preferably denotes 0 or 1.

m preferably denotes 0, 1 or 2.

The invention preferably relates to a process according to claim 1 for the preparation of compounds of the formula I in which $R^1$ denotes $NO_2$, CN, $COOR^3$, $COR^3$ or Cl, $R^2$ denotes H, Hal or A.

Preference is furthermore given to a process according to claim 1 or 2 for the preparation of compounds of the formula I in which $R^1$ denotes $NO_2$, CN, $COOR^3$, $CON(R^3)_2$, $COR^3$, $SO_2R^4$, $SO_2N(R^3)_2$, $CF_3$, F or Cl, $R^2$ denotes H, Hal or A, $R^3$ denotes H, A, —$[C(R^5)_2]_n$—Ar or -$[C(R^5)_2]_n$-Het.

Preference is furthermore given to a process according to claim 1 for the preparation of compounds of the formula I in which Ar denotes phenyl.

Preference is furthermore given to a process for the preparation of compounds of the formula I in which $R^4$ denotes A.

Preference is furthermore given to a process for the preparation of compounds of the formula I in which $R^1$ denotes $NO_2$, CN, $COOR^3$, $CON(R^3)_2$, $COR^3$, $CF_3$, F or Cl, $R^2$ denotes H, Hal or A', $R^3$ denotes H, A' or -$[C(R^5)_2]_n$—Ar, Ar denotes phenyl, $R^5$ denotes H or A', A' denotes unbranched or branched alkyl having 1-6 C atoms, Hal denotes F, Cl, Br or I, n denotes 0, 1 or 2.

Very particular preference is given to a process according to claim 1 for the preparation of compounds selected from the group 4-(4-nitrophenyl)-3-oxomorpholine,
4-(3-nitrophenyl)-3-oxomorpholine,
4-(2-nitrophenyl)-3-oxomorpholine,
2-methyl-4-(4-nitrophenyl)-3-oxomorpholine,
4-(4-methoxycarbonylphenyl)-3-oxomorpholine,
4-(4-benzoylphenyl)-3-oxomorpholine.

Preference is furthermore given to a process according to one or more of claims 1-6 for the preparation of compounds of the formula I in which the amine of the formula II has a $pK_a$ value $\leq 3$.

The compounds of the formula I can preferably be obtained by, in a first step a), reacting compounds of the formula II with 5-chloro-2,3-dihydro-1,4-dioxin to give a compound of the formula III.

The reaction is generally carried out in an inert solvent, but can also be carried out without solvent in mass.

It is advantageous to add an acid, for example a Brönsted acid, such as hydrochloric acid, or a Lewis acid, or alternatively to add 2,2-dichlorodioxene, a compound which, as is known from the literature (R. K. Summerbell, H. E. Lunk, J. Am. Chem. Soc. 79, p. 4802, 1957), readily dissociates into hydrogen chloride and 2-chlorodioxene.

Depending on the conditions used, the reaction time is between a few minutes and 14 days, preferably between one and ten hours, the reaction temperature is between about 0° and 150°, normally between 20° and 130°, preferably between 60° and 110°, very particularly preferably between 70° and 90° C.

Suitable inert solvents are, for example, water; hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether (methyl glycol or ethyl glycol), ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to acetonitrile.

In a second step b), compounds of the formula III are cyclised to give the compounds of the formula I.

The reaction is generally carried out in an inert solvent, preferably in the presence of an alkali or alkaline earth metal hydroxide, carbonate or bicarbonate. Very particular preference is given to weak bases, such as caesium carbonate or potassium carbonate.

Depending on the conditions used, the reaction time is between a few minutes and 14 days, preferably between one and twenty hours, the reaction temperature is between about 0° and 150°, normally between 0° and 90°, preferably between 10° and 70°, particularly preferably between 20° and 50° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether (methyl glycol or ethyl glycol), ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents, particular preference is given to acetonitrile.

Process steps a) and b) can also be carried out as a one-pot reaction. When the amine and 2-chlorodioxene have reacted completely, the temperature of the solution is lowered and an excess of alkali metal carbonate (typically 1.5 to 4 equivalents) is added and the reaction mixture is stirred until conversion is complete.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

The invention also relates to the intermediate compounds of the formula III

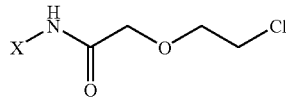

III in which
X denotes

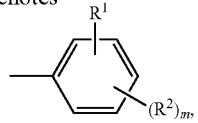

$R^1$ denotes $NO_2$ or CN,
$R^2$ denotes H, Hal, A, $OR^3$, $N(R^3)_2$, $NO_2$, CN, $COOR^3$, $CON(R^3)_2$, $NR^3COA$, $NR^3CON(R^3)_2$, $NR^3COOR^3$, $NR^3SO_2A$, —[C(R^5)_2]_n—Ar, —[C(R^5)_2]_n-Het, —[C(R^5)_2]_n-cycloalkyl, $COR^3$, $SO_2N(R^3)_2$ or $SO_2R^4$,
$R^3$ denotes H, A, —[C(R^5)_2]_n—Ar or —[C(R^5)_2]_n-Het,
$R^4$ denotes A, —[C(R^5)_2]_n—Ar or —[C(R^5)_2]_n-Het,
$R^5$ denotes H or A',
Ar denotes phenyl which is unsubstituted or mono-, di- or trisubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ or $S(O)_nA$,
Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O),
A' denotes unbranched or branched alkyl having 1-6 C atoms,
A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F,
Hal denotes F, Cl, Br or I,
n denotes 0, 1 or 2,
m denotes 0, 1, 2, 3 or 4, and salts thereof.

The intermediate compounds are important for the preparation of the compounds of the formula I.

The preferred meanings of the radicals correspond to those as indicated above, unless expressly stated otherwise.

The invention also relates to the intermediate compounds in which
$R^1$ denotes $NO_2$ or CN,
$R^2$ denotes H, Hal or A, and salts thereof.

Preference is furthermore given to intermediate compounds in which
$R^1$ denotes $NO_2$ or CN,
$R^2$ denotes H, Hal or A,
$R^3$ denotes H, A, —[C(R^5)_2]_n—Ar or —[C(R^5)_2]_n-Het, and salts thereof.

Preference is furthermore given to intermediate compounds in which
Ar denotes phenyl, and salts thereof.

Preference is furthermore given to intermediate compounds in which
$R^4$ denotes A, and salts thereof.

Particular preference is given to intermediate compounds in which
$R^1$ denotes $NO_2$ or CN,
$R^2$ denotes H, Hal or A',
$R^3$ denotes H, A' or —[C(R^5)_2]_n—Ar,
Ar denotes phenyl,
$R^5$ denotes H or A',
A' denotes unbranched or branched alkyl having 1-6 C atoms,
Hal denotes F, Cl, Br or I,
n denotes 0, 1 or 2,
m denotes 0, 1 or 2, and salts thereof.

Particular preference is given to intermediate compounds in which
$R^1$ denotes $NO_2$,
$R^2$ denotes H, Hal or A',
$R^3$ denotes H, A' or $—[C(R^5)_2]_n—Ar$,
Ar denotes phenyl,
$R^5$ denotes H or A',
A' denotes unbranched or branched alkyl having 1-6 C atoms,
Hal denotes F, Cl, Br or I,
n denotes 0, 1 or 2,
m denotes 0, 1 or 2, and salts thereof.

The invention also relates to a process for the preparation of intermediate compounds of the formula III

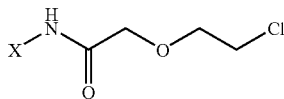  III in which
X denotes

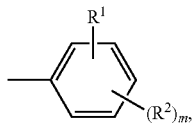

$R^1$ denotes $NO_2$, CN, $COOR^3$, $CON(R^3)_2$, $COR^3$, $SO_2R^4$, $SO_2N(R^3)_2$, $CF_3$, F or Cl,
$R^2$ denotes H, Hal, A, $OR^3$, $N(R^3)_2$, $NO_2$, CN, $COOR^3$, $CON(R^3)_2$, $NR^3COA$, $NR^3CON(R^3)_2$, $NR^3COOR^3$, $NR^3SO_2A$, $—[C(R^5)_2]_n—Ar$, $—[C(R^5)_2]_n$-Het, $—[C(R^5)_2]_n$-cycloalkyl, $COR^3$, $SO_2N(R^3)_2$ or $SO_2R^4$,
$R^3$ denotes H, A, $—[C(R^5)_2]_n—Ar$ or $—[C(R^5)_2]_n$-Het,
$R^4$ denotes A, $—[C(R^5)_2]_n—Ar$ or $—[C(R^5)_2]_n$-Het,
$R^5$ denotes H or A',
Ar denotes phenyl which is unsubstituted or mono-, di- or trisubstituted By Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ or $S(O)_nA$,
Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O),
A' denotes unbranched or branched alkyl having 1-6 C atoms,
A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F,
Hal denotes F, Cl, Br or I,
n denotes 0, 1 or 2,
m denotes 0, 1, 2, 3 or 4, and salts thereof, characterised in that a) a compound of the formula II

 II in which
X has the meaning indicated above,
is reacted with 5-chloro-2,3-dihydro-1,4-dioxin

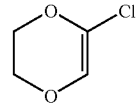

and
the compound of the formula III is optionally converted into its salt.

The conditions of the process, in particular the preferred ones, are the same as indicated under the process for the preparation of the compound of the formula I.

The preferred meanings of the radicals correspond to those as indicated above, unless expressly stated otherwise.

Preference is given to a process for the preparation of intermediate compounds of the formula III in which
$R^1$ denotes $NO_2$ or CN,
$R^2$ denotes H, Hal, A, $OR^3$, $N(R^3)_2$, $NO_2$, CN, $COOR^3$, $CON(R^3)_2$, $NR^3COA$, $NR^3CON(R^3)_2$, $NR^3COOR^3$, $NR^3SO_2A$, $—[C(R^5)_2]_n—Ar$, $—[C(R^5)_2]_n$-Het, $—[C(R^5)_2]_n$-cycloalkyl, $COR^3$, $SO_2N(R^3)_2$ or $SO_2R^4$,
$R^3$ denotes H, A, $—[C(R^5)_2]_n—Ar$ or $—[C(R^5)_2]_n$-Het,
$R^4$ denotes A, $—[C(R^5)_2]_n—Ar$ or $—[C(R^5)_2]_n$-Het,
$R^5$ denotes H or A',
Ar denotes phenyl which is unsubstituted or mono-, di- or trisubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ or $S(O)_nA$,
Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O),
A' denotes unbranched or branched alkyl having 1-6 C atoms,
A denotes unbranched, branched or cyclic alkyl having 1-12 C atoms, in which one or two $CH_2$ groups may be replaced by O or S atoms and/or A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F,
Hal denotes F, Cl, Br or I,
n denotes 0, 1 or 2,
m denotes 0, 1, 2, 3 or 4.

and salts thereof.

The intermediate compounds are important for the preparation of the compounds of the formula I.

The preferred meanings of the radicals correspond to those as indicated above, unless expressly stated otherwise.

The invention also relates to the intermediate compounds in which
$R^1$ denotes $NO_2$ or CN,
$R^2$ denotes H, Hal or A, and salts thereof.

Preference is furthermore given to intermediate compounds in which
$R^1$ denotes $NO_2$ or CN,
$R^2$ denotes H, Hal or A,
$R^3$ denotes H, A, —$[C(R^5)_2]_n$-Het, and salts thereof.
Preference is furthermore given to intermediate compounds in which
Ar denotes phenyl, and salts thereof.
Preference is furthermore given to intermediate compounds in which
$R^4$ denotes A, and salts thereof.
Particular preference is given to intermediate compounds in which
$R^1$ denotes $NO^2$ or CN,
$R^2$ denotes H, Hal or A',
$R^3$ denotes H, A' or —$[C(R^5)_2]_n$—Ar,
Ar denotes phenyl,
$R^5$ denotes H or A',
A' denotes unbranched or branched alkyl having 1-6 C atoms,
Hal denotes F, Cl, Br or I,
n denotes 0, 1 or 2,
m denotes 0, 1 or 2, and salts thereof.
Particular preference is given to intermediate compounds
$R^1$ denotes $NO^{2,}$
$R^2$ denotes H, Hal or A',
$R^3$ denotes H, A' or —$[C(R^5)_2]_n$—Ar,
Ar denotes phenyl,
$R^5$ denotes H or A',
A' denotes unbranched or branched alkyl having 1-6 C atoms,
Hal denotes F, Cl, Br or I,
n denotes 0, 1 or 2,
m denotes 0, 1 or 2, and salts thereof.
The invention also relates to a process for the preparation of intermediate compounds of the formula III

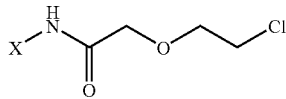

III in which

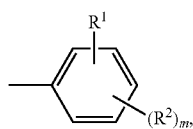

X denotes
$R^1$ denotes $NO^2$, CN, $COOR^3$, $CON(R^3)_2$, $COR^3$, $SO_2R^4$, $SO_2N(R^3)_2$, $CF_3$, F or Cl,
$R^2$ denotes H, Hal, A, $OR^3$, $N(R^3)_2$, $NO_2$, CN, $COOR^3$, $CON(R_3)_2$, $NR^3COA$, $NR^3CON(R^3)_2$, $NR^3COOR^3$, $NR^3SO_2A$, —$[C(R^5)_2]_n$—Ar, —$[C(R^5)_2]_n$—Het, —$[C(R^5)_2]_n$-cycloalkyl, $COR^3$, $SO_2N(R^3)_2$ or $SO_2R^4$,
$R^3$ denotes H, A, —$[C(R^5)_2]_{n\text{-}Ar}$ or —$[C(R^5)_2]_n$-Het,
$R^4$ denotes A, —$[C(R^5)_2]_n$—Ar or —$[C(R^5)_2]_{n\text{-}Het}$,
$R^5$ denotes H or A',
Ar denotes phenyl which is unsubstituted or mono-, di- or trisubstituted by Hal, A, $OR^5$, $N(R^5)_2$, $NO_2$, CN, $COOR^5$, $CON(R^5)_2$, $NR^5SO_2A$, $NR^5SO_2A$, $COR^5$, $SO_2N(R^5)_2$ or $S(O)_nA$,
Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O),
A' denotes unbranched or branched alkyl having 1-6 C atoms,
A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F,
Hal denotes F, Cl , Br or I,
n denotes 0, 1 or 2,
m denotes 0,1,2,3or 4, and salts thereof, characterised in that
a) a compound of the formula II

X—$NH_2$  II in which
X has the meaning indicated above, is reacted with 5-chloro-2,3-dihydro-1 ,4-dioxin

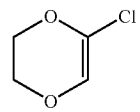

and the compound of the formula III is optionally converted into its salt.
The conditions of the process, in particular the preferred ones, are the same as indicated under the process for the preparation of the compound of the formula I.
The preferred meanings of the radicals correspond to those as indicated above, unless expressly stated otherwise.
Preference is given to a process for the preparation of intermediate compounds of the formula III in which
$R^1$ denotes $NO_2$ or CN,
$R^2$ denotes H, Hal, A, $OR^3$, $N(R^3)_2$, $NO_2$, CN, $COOR^3$, $CON(R^3)_2$, $NR^3COA$, $NR^3CON(R^3)_2$, $NR^3COOR^3$, $NR^3SO_2A$, —$[C(R^5)_2]_n$—Ar, —$[C(R^5)_2]_n$-Het, —$[C(R^5)_2]_n$-cycloalkyl, $COR^3$, $SO_2N(R^3)_2$ or $SO_2R^4$,
$R^3$ denotes H, A, —$[C(R^5)_2]_n$—Ar or —$[C(R^5)_2]_n$-Het,
$R^4$ denotes A, —$[C(R^5)_2]_n$—Ar or —$[C(R^5)_2]_n$-Het,
$R^5$ denotes H or A',
Ar denotes phenyl which is unsubstituted or mono-, di- or trisubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_n2$ or $S(O)_nA$,
Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/or carbonyl oxygen (=O),
A' denotes unbranched or branched alkyl having 1-6 C atoms, A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F, Hal denotes F, Cl, Br or I, n denotes 0, 1 or 2, m denotes 0, 1, 2, 3or 4.

Preference is furthermore given to a process for the preparation of intermediate compounds of the formula III in which $R^1$ denotes $NO_2$ or CN, $R^2$ denotes H, Hal or A.

Preference is furthermore given to a process for the preparation of intermediate compounds of the formula III in which $R^1$ denotes $NO_2$ or CN, $R^2$ denotes H, Hal or A, $R^3$ denotes H, A, —[C(R^5)_2]_n—Ar or —[C(R^5)_2]_n-Het.

Preference is furthermore given to a process for the preparation of intermediate compounds of the formula III in which Ar denotes phenyl.

Preference is also given to a process for the preparation of intermediate compounds of the formula III in which $R^4$ denotes A.

Particular preference is given to a process for the preparation of intermediate compounds of the formula III in which $R^1$ denotes $NO_2$ or CN, $R^2$ denotes H, Hal or A', $R^3$ denotes H, A' or —[C(R^5)_2]_n—Ar, Ar denotes phenyl, $R^5$ denotes H or A', A' denotes unbranched or branched alkyl having 1-6 C atoms, Hal denotes F, Cl, Br or I, n denotes 0, 1 or 2, m denotes 0, 1 or 2.

Above and below, all temperatures are indicated in °C. Mass spectrometry (MS): EI (electron impact ionisation) $M^+$; ESI (electrospray ionisation) $(M+H)^+$; FAB (fast atom bombardment) $(M+H)^+$ Example 1

4-(4-Nitrophenyl)-3-oxomorpholine

The preparation is carried out analogously to the following scheme:

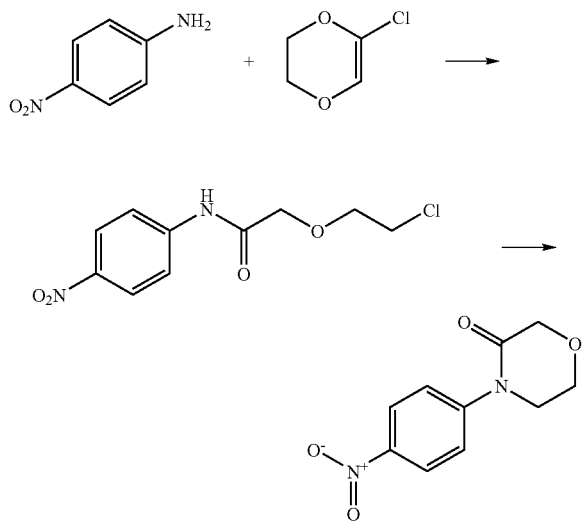

1.1 without solvent:

1.53 g of a mixture of 2-chlorodioxene and 2,2-dichlorodioxane (molar ratio 1:1) are added to 1.00 g (7.24 mmol) of 4-nitroaniline, and the mixture is heated to 80° C. with stirring. A solid brown mass forms within one hour and becomes liquid again and crystallises within the following 12 hours. The crude product is recrystallised from ethanol with addition of water, giving 1.80 g of 2-(2-chloroethoxy)-N-(4-nitrophenyl)acetamide ("A1") as yellowish crystals, m.p. 101-102° C. $^1$H-NMR ($d^6$-DMSO): δ=3.82 (m; 4H), 4.23 (s; 2H), 7.91 (d, J=9 Hz, 2H), 8.23 (d, J=9 Hz, 2H), 10.34 (s, 1H).

1.2 in acetonitrile:

310 mg of a mixture of 2-chlorodioxene and 2,2-dichlorodioxane (molar ratio 1:1) are added to a solution of 276 mg (2.00 mmol) of 4-nitroaniline in 2 ml of acetonitrile, and the solution is heated at 80° C. with stirring for 18 hours. The reaction mixture is evaporated, and the residue is recrystallised from ethanol/water: 360 mg of "A1" as yellowish crystals.

1.3 1 kg of "A1" is dissolved in 5 liters of acetonitrile at room temperature, 835 g of potassium carbonate are added, and the mixture is stirred at this temperature for 18 hours. The mixture is warmed to 50° and worked up analogously to Example 6, giving 4-(4-nitrophenyl)-3-oxomorpholine ("A2"), m.p. 150-152°.

Example 2

4-(4-Nitro-2-methylphenyl)-3-oxomorpholine 1.05 g of a mixture of 2-chlorodioxene and 2,2-dichlorodioxane (molar ratio 1:1) are added to a solution of 1.10 g (7.24 mmol) of 2-methyl-4-nitroaniline in 20 ml of THF, and the mixture is heated to the boil. The solvent is distilled off, and the residue, a brown viscous liquid, is heated at 80° C. for 18 hours. After cooling, the residue is recrystallised from toluene/tert-butyl methyl ether: 1.50 g of 2-(2-chloroethoxy)-N-(2-methyl-4-nitrophenyl)acetamide as yellowish crystals, m.p. 113-114° C. $^1$H-NMR ($d^6$-DMSO): δ=2.35 (s; 3H), 3.82 (m; 4H), 4.23 (s; 2H), 8.05 (d, J=8 Hz, 1H) 8.09 (dd, J=9 Hz, J=1 Hz, 1H), 8.16 (d, J=1 Hz, 1H), 9.33 (s, 1H).

The cyclisation is carried out analogously to 1.3, giving 4-(4-nitro-2-methylphenyl)-3-oxomorpholine, ESI 237.

Example 3

4-(2-Nitrophenyl)-3-oxomorpholine 1.12 g of a mixture of 2-chlorodioxene and 2,2-dichlorodioxane (molar ratio 89:11) are added to 1.12 g (8.12 mmol) of 2-nitroaniline, and the mixture is heated to 80° C. with stirring. A viscous liquid forms, which is stirred for 3 hours. On cooling to room temperature, the product crystallises: 2.1 g of 2-(2-chloroethoxy-N-(2-nitrophenyl)acetamide as yellowish crystals. $^1$H-NMR ($d^6$-DMSO): δ=3.84 (m; 4H), 4.25 (s; 2H), 7.35 (t, J=8 Hz, 1H), 7.77 (t, J=8 Hz, 1H), 8.14 (d, J=8 Hz, 1H), 8.30 (d, J=8 Hz, 1H), 10.74 (s, 1H).

The cyclisation is carried out analogously to 1.3, giving 4-(2-nitrophenyl)-3-oxomorpholine, ESI 223.

Example 4

4-(4-Cyanophenyl)-3-oxomorpholine

A mixture of 959 mg (8.12 mmol) of 4-aminobenzonitrile and 1.12 g of a mixture of 2-chlorodioxene and 2,2-dichlorodioxane (molar ratio 89:11) is heated at 80° C. with stirring for 18 hours. On cooling to room temperature, the product crystallises: 1.9 g of 2-(2-chloroethoxy)-N-(4-cyanophenyl) acetamide as yellowish crystals. $^1$H-NMR (d 6-DMSO): δ=3.82 (m; 4H), 4.19 (s; 2H), 7.78 (d, J=8 Hz, 2H), 7.85 (d, J=8 Hz, 2H), 10.22 (s, 1H).

The cyclisation is carried out analogously to 1.3, giving 4-(4-cyanophenyl)-3-oxomorpholine, ESI 203.

Example 5

4-(4-Methoxycarbonylphenyl)-3-oxomorpholine

A mixture of 1.23 mg (8.12 mmol) of methyl 4-aminobenzoate and 1.12 g of a mixture of 2-chlorodioxene and 2,2-dichlorodioxane (molar ratio 89:11) is heated at 80° C. with stirring for 18 hours. On cooling to room temperature, the product crystallises: 2.2 g of methyl 4-[2-(2-chloroethoxy) acetylamino]benzoate as yellowish crystals. $^1$H-NMR (d$^6$-DMSO): δ=3.82 (m; 7H), 4.20 (s; 2H), 7.82 (d, J=8 Hz, 2H), 7.93 (d, J=8 Hz, 2H), 10.15 (s, 1H).

The cyclisation is carried out analogously to 1.3, giving 4-(4-methoxycarbonylphenyl)-3-oxomorpholine, ESI 236.

Example 6

One-Pot Reaction for the Preparation of "A2"

6.40 g of 2-chlorodioxene (contains 6% of 2,2-dichlorodioxane) are added to a solution of 6.00 g (24.9 mmol) of 4-nitroaniline in 40 ml of acetonitrile, and the mixture is stirred at 80° C. for 18 hours. The reaction solution is cooled to 40° C., 18.0 g (130 mmol) of potassium carbonate are added, and the mixture is stirred at this temperature for 14 hours. The reaction mixture is filtered, the residue is washed well with acetonitrile, and the filtrate is evaporated. The residue is recrystallised from acetonitrile: 8.2 g of brownish crystals ("A2"), m.p. 150-152° C. $^1$H-NMR (d$^6$-DMSO): δ=3.86 (t, J=5 Hz; 2H), 4.02 (t, J=5 Hz; 2H), 4.28 (s; 2H), 7.77 (d, J=9 Hz, 2H), 8.28 (d, J=9 Hz, 2H).

Example 7

4-(3-Nitrophenyl)-3-oxomorpholine

A mixture of 1.12 g (8.12 mmol) of 3-nitroaniline and 1.11 g of 2-chlorodioxene (contains 6% of 2,2-dichlorodioxane) is heated at 80° C. with stirring for 24 hours, giving 2.1 g of 2-(2-chloroethoxy)-N-(3-nitrophenyl)acetamide as brownish oil. ESI 259.

The cyclisation is carried out analogously to 1.3, giving 4-(3-nitrophenyl)-3-oxomorpholine, ESI 223.

Example 8

4-(4-Benzoylphenyl)-3-oxomorpholine

A mixture of 1.60 g (8.12 mmol) of 4-aminobenzophenone and 1.11 g of 2-chlorodioxene (contains 6% of 2,2-dichlorodioxane) is heated at 80° C. with stirring for 24 hours, giving 2.6 g of N-(4-benzoylphenyl)-2-(2-chloroethoxy)acetamide as brown oil. ESI 318.

The cyclisation is carried out analogously to 1.3, giving 4-(4-benzoylphenyl)-3-oxomorpholine, ESI 282.

Example 9

4-(3-Fluorophenyl)-3-oxomorpholine

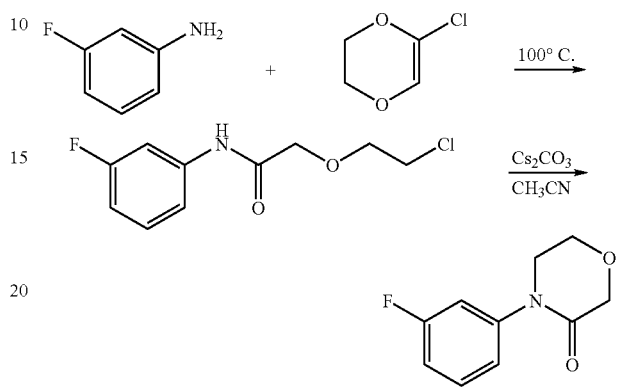

A mixture of 12.0 g (108 mmol) of 3-fluoraniline and 16 g of 2-chlorodioxene (contains 6% of 2,2-dichlorodioxane) is heated at 100° C. for 24 hours. The mixture is allowed to cool, and excess 2-chlorodioxene is removed under reduced pressure, giving 25 g of 2-(2-chloroethoxy)-N-(3-fluorophenyl) acetamide as brown oil; ESI 232. This oil is dissolved in 400 ml of acetonitrile, and 84.7 g (260 mmol) of caesium carbonate are added. The suspension formed is stirred at room temperature for 18 hours. The reaction mixture is filtered, and the filtrate is evaporated, giving 21.0 g of 4-(3-fluorophenyl) morpholin-3-one as brown oil; ESI 196. $^1$H-NMR (d$^6$-DMSO): δ=3.77 (t, J=5 Hz; 2H), 3.97 (t, J=5 Hz; 2H), 4.23 (s; 2H), 7.11 (dddd, $J_1$=8 Hz, $J_2$=8 Hz, $J_3$=2 Hz, $J_4$=0.5 Hz, 1H), 7.26 (ddd, $J_1$=8 Hz, $J_2$=2 Hz, $J_3$=0.5 Hz, 1H), 7.34 (ddd, $J_1$=10 Hz, $J_2$=2 Hz, $J_3$=2 Hz, 1H), 7.45 (ddd, $J_1$=8 Hz, $J_2$=8 Hz, $J_3$=7 Hz, 1H).

Example 10

4-(3-Methyl-4-nitrophenyl)-3-oxomorpholine

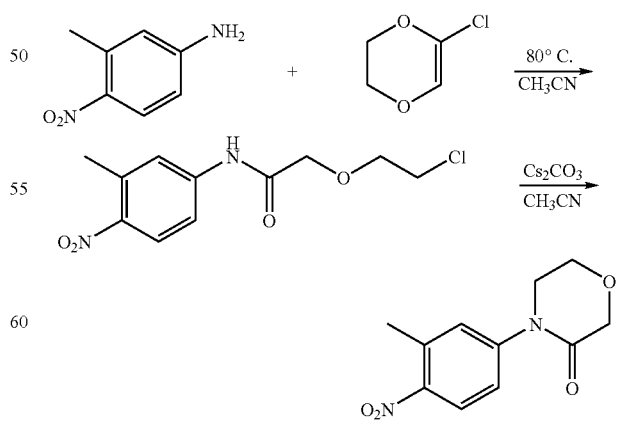

12.8 g of 2-chlorodioxene (contains 6% of 2,2-dichlorodioxane) are added to a solution of 10.0 g (65.7 mmol) of 3-methyl-4-nitroaniline in 250 ml of acetonitrile, and the mixture is stirred at 80° C. for 66 hours. The reaction solution is cooled to room temperature, 42.8 g (131 mmol) of caesium carbonate are added, and the mixture is stirred at room temperature for 18 hours. The reaction mixture is filtered, the residue is washed well with acetonitrile, and the filtrate is evaporated. The residue is recrystallised from a little acetonitrile, giving 12.8 g (83%) of 4-(3-methyl-4-nitrophenyl)morpholin-3-one as yellowish solid. ESI 236. $^1$H-NMR (d$^6$-DMSO): δ=2.54 (s; 2H), δ=3.82 (t, J=5 Hz; 2H), 4.00 (t, J=5 Hz; 2H), 4.25 (s; 2H), 7.57 (m; 2H), 8.04 (d, J.=8 Hz; 1H).

4-(2-Chloro-5-fluoro-4-nitrophenyl)-3-oxomorpholine is obtained analogously

Example 11

4-(2-Bromo-5-nitrophenyl)-3-oxomorpholine is obtained analogously to Example 7

4-(2-Methoxycarbonyl-5-nitrophenyl)-3-oxomorpholine is obtained analogously to Example 7

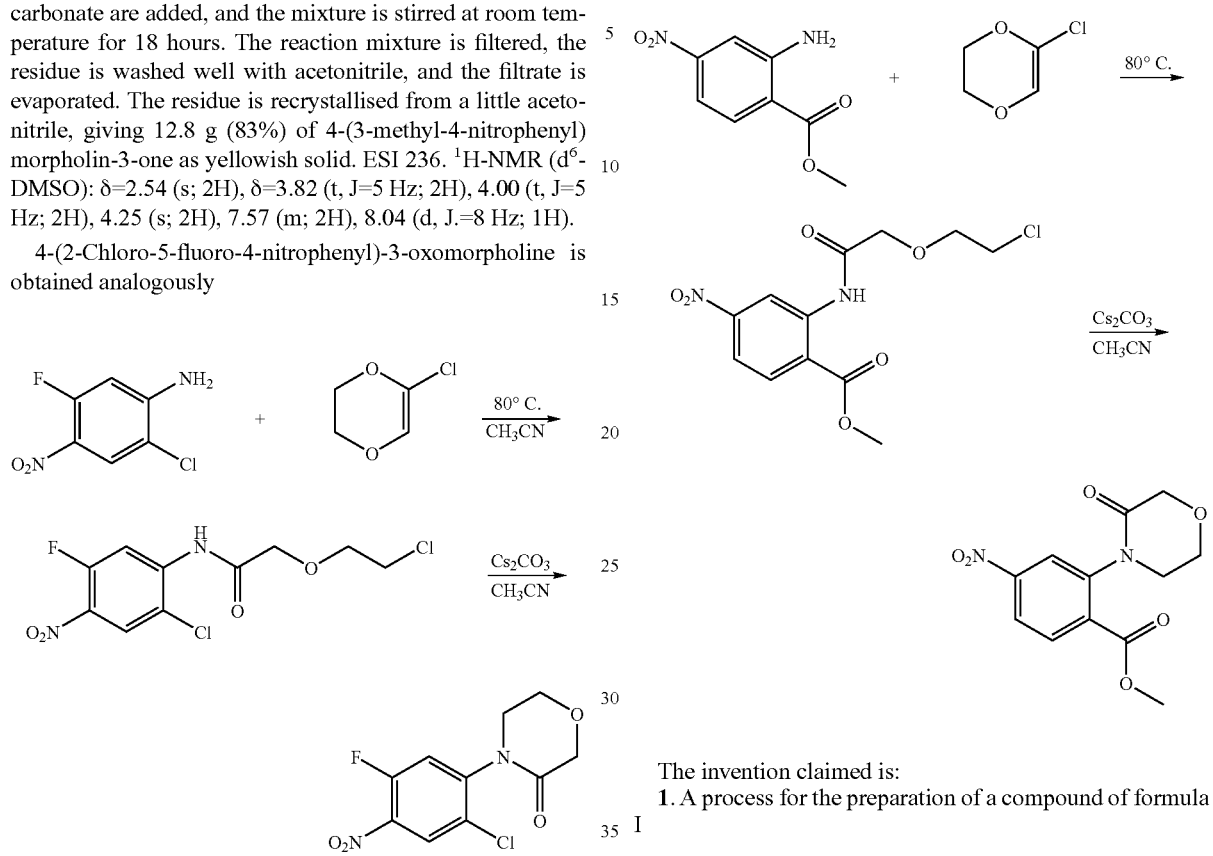

The invention claimed is:
1. A process for the preparation of a compound of formula I

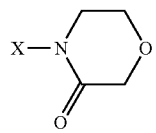

in which
X denotes

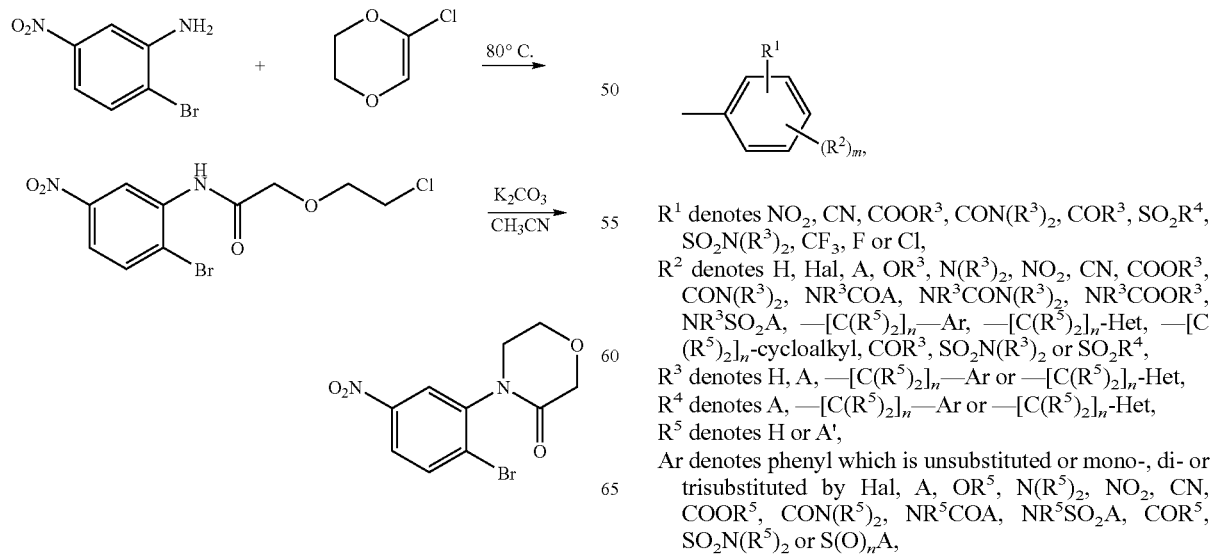

R$^1$ denotes NO$_2$, CN, COOR$^3$, CON(R$^3$)$_2$, COR$^3$, SO$_2$R$^4$, SO$_2$N(R$^3$)$_2$, CF$_3$, F or Cl,
R$^2$ denotes H, Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$COOR$^3$, NR$^3$SO$_2$A, —[C(R$^5$)$_2$]$_n$—Ar, —[C(R$^5$)$_2$]$_n$-Het, —[C(R$^5$)$_2$]$_n$-cycloalkyl, COR$^3$, SO$_2$N(R$^3$)$_2$ or SO$_2$R$^4$,
R$^3$ denotes H, A, —[C(R$^5$)$_2$]$_n$—Ar or —[C(R$^5$)$_2$]$_n$-Het,
R$^4$ denotes A, —[C(R$^5$)$_2$]$_n$—Ar or —[C(R$^5$)$_2$]$_n$-Het,
R$^5$ denotes H or A',
Ar denotes phenyl which is unsubstituted or mono-, di- or trisubstituted by Hal, A, OR$^5$, N(R$^5$)$_2$, NO$_2$, CN, COOR$^5$, CON(R$^5$)$_2$, NR$^5$COA, NR$^5$SO$_2$A, COR$^5$, SO$_2$N(R$^5$)$_2$ or S(O)$_n$A, Het denotes a mono- or bicyclic saturated, unsaturated or aromatic heterocycle having 1 to 4 N, O and/or S atoms which is unsubstituted or mono- or disubstituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$, $S(O)_nA$ and/ or carbonyl oxygen (=O), A' denotes unbranched or branched alkyl having 1-6 C atoms, A denotes unbranched, branched or cyclic alkyl having 1-12 C atoms, in which one or two $CH_2$ groups may be replaced by O or S atoms and/or by —CH=CH— groups and/or in addition 1-7H atoms may be replaced by F, Hal denotes F, Cl, Br or I, n denotes 0, 1 or 2, m denotes 0, 1, 2, 3 or 4, and salts thereof, characterised in that a) a compound of the formula II which has a $pK_a$ value $\leq 3$

                II in which

X has the meaning indicated above, is reacted with 5-chloro-2,3-dihydro-1,4-dioxin

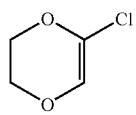

to give a compound of the formula III

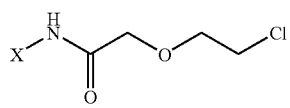                III in which

X has the meaning indicated above, b) then a compound of the formula III is cyclised to give a compound of the formula I, and c) the latter is optionally converted into its salt by converting a base or acid of the formula I into one of its salts.

2. A process according to claim 1 for the preparation of a compound of formula I in which $R^1$ denotes $NO_2$, CN, $COOR^3$, $COR^3$ or Cl, $R^2$ denotes H, Hal or A, and salts thereof.

3. A process according to claim 1 for the preparation of a compound of formula I in which $R^1$ denotes $NO_2$, CN, $COOR^3$, $CON(R^3)_2$, $COR^3$, $SO_2R^4$, $SO_2N(R^3)_2$, $CF_3$, F or Cl, $R^2$ denotes H, Hal or A, $R^3$ denotes H, A, —$[C(R^5)_2]_n$—Ar or —$[C(R^5)_2]_n$-Het, and salts thereof.

4. A process according to claim 1 for the preparation of a compound of the formula I in which Ar denotes phenyl, and salts thereof.

5. A process according to claim 1 for the preparation of a compound of the formula I in which $R^4$ denotes A, and salts thereof.

6. A process according to claim 1 for the preparation of a compound of the formula I in which $R^1$ denotes $NO_2$, CN, $COOR^3$, $CON(R^3)_2$, $COR^3$, $CF_3$, F or Cl, $R^2$ denotes H, Hal or A', $R^3$ denotes H, A' or —$[C(R^5)_2]_n$—Ar, Ar denotes phenyl, $R^5$ denotes H or A', A' denotes unbranched or branched alkyl having 1-6 C atoms, Hal denotes F, Cl, Br or I, n denotes 0, 1 or 2, and salts thereof.

7. A process according to claim 1 in which process steps a) and b) are carried out as a one-pot reaction.

8. A process according to claim 1, in which process step a) is carried out at a temperature between 0 and 150° C.

9. A process according to claim 8, in which process step a) is carried out at a temperature between 70 and 90° C.

10. A process according to claim 1, in which the cyclization is carried out in an inert solvent or solvent mixture, in the presence of an alkali or alkaline earth metal hydroxide, carbonate or bicarbonate.

11. A process according to claim 1, in which the cyclization is carried out in the presence of caesium carbonate or potassium carbonate.

12. A process according to claim 1, in which the process is carried out as a one-pot reaction in acetonitrile.

13. A process according to claim 1 for the preparation of 4-(4-nitrophenyl)-3-oxomorpholine, 4-(3-nitrophenyl)-3-oxomorpholine, 4-(2-nitrophenyl)-3-oxomorpholine, 2-methyl-4-(4-nitrophenyl)-3-oxomorpholine, 4-(4-methoxycarbonylphenyl)-3-oxomorpholine, 4-(4-benzoylphenyl)-3-oxomorpholine, or a salts thereof.

* * * * *